(12) United States Patent
Braunstein

(10) Patent No.: US 7,476,026 B2
(45) Date of Patent: Jan. 13, 2009

(54) METHOD AND APPARATUS FOR CALIBRATING X-RAY DETECTORS IN A CT-IMAGING SYSTEM

(75) Inventor: David Braunstein, Nesher (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 933 days.

(21) Appl. No.: 10/491,175

(22) PCT Filed: Oct. 1, 2001

(86) PCT No.: PCT/IL01/00919

§ 371 (c)(1),
(2), (4) Date: Mar. 30, 2004

(87) PCT Pub. No.: WO03/028554

PCT Pub. Date: Apr. 10, 2003

(65) Prior Publication Data

US 2004/0199065 A1    Oct. 7, 2004

(51) Int. Cl.
*G01D 18/00* (2006.01)

(52) U.S. Cl. ............................. 378/207; 378/19
(58) Field of Classification Search ............... 378/4, 378/19, 207; 250/252.1, 363.09
See application file for complete search history.

(56) References Cited

U.S. PATENT DOCUMENTS 5,450,461 A * 9/1995 Hsieh ............................ 378/19
5,825,843 A * 10/1998 Kobayashi .................... 378/20

* cited by examiner

*Primary Examiner*—Jurie Yun

(57) ABSTRACT

A method of adjusting values for sensitivities of X-ray detectors comprised in a CT-imager that generate signals responsive to X-rays from an X-ray source in the imager, comprising: acquiring signals generated by X-ray detectors in the CT-imager responsive to X-rays incident thereon from the X-ray source for views taken during a scanning procedure performed by the CT-imager to image a patient when only air is present in a space between the X-ray source and the detectors; and using the signals to adjust the values of the sensitivities.

13 Claims, 3 Drawing Sheets

METHOD AND APPARATUS FOR CALIBRATING X-RAY DETECTORS IN A CT-IMAGING SYSTEM

FIELD OF THE INVENTION

The present invention relates to computerized tomography (CT) X-ray imaging, and in particular to methods for calibrating X-ray detectors comprised in a CT-imaging system.

BACKGROUND OF THE INVENTION

In CT X-ray imaging of a patient, X-rays are used to image internal structure and features of a region of the patient's body. The imaging is performed by a CT-imaging system, hereinafter referred to as a "CT-imager", which images internal structure and features of a plurality of contiguous relatively thin planar slices of the body region using X-rays.

The CT-imager generally comprises an X-ray source that provides a planar, fan-shaped X-ray beam and an array of X-ray detectors that are coplanar with the fan beam and face the X-ray source. The X-ray source and array of detectors are mounted in a gantry so that a patient being imaged with the imager, generally lying on an appropriate support couch, can be positioned in a space within the gantry between the X-ray source and the array of detectors. The gantry and couch are moveable relative to each other so that the X-ray source and detector array can be positioned axially at desired locations along the patient's body.

The gantry comprises a stationary structure referred to as a stator and a rotary element, referred to as a rotor, which is mounted to the stator so that the rotor is rotatable about the axial direction. Angular position of the rotor about the axial direction is controllable so that the X-ray source can be positioned at desired angles, referred to as "view angles", around the patient's body.

To image a slice in a region of a patient's body, the X-ray source is positioned at the axial position of the slice and the X-ray source is rotated around the slice to illuminate the slice with X-rays from a plurality of different view angles. At each view angle, detectors in the array of detectors generate signals that are measures of intensities of X-rays from the source that pass through the slice. The intensity of X-rays measured by a particular detector in the array of detectors is a function of an amount by which X-rays are attenuated by material in the slice along a path length from the X-ray source, through the slice, to the particular detector. The measurement provides information on composition and density of tissue in the slice along the path-length.

For example, if incident X-ray intensity sensed by an "n-th" detector in the array of detectors when the X-ray source is located at a view angle $\theta$ is represented by $I(n,\theta)$, then $I(n,\theta)=I_o\exp(-\int\mu(l)dl)$. In the expression for $I(n,\theta)$, $I_o$ is intensity of X-rays with which the X-ray source illuminates the slice, integration over l represents integration over a path through material in the slice along a direction from the X-ray source to the n-th detector and $\mu(l)$ is an absorption coefficient for X-rays per unit path-length in the material at position l along the path. (Dependence of the integral on n and $\theta$ is not shown explicitly and is determined through dependence of the length and direction of the path-length l on n and $\theta$.) Intensity $I_o$ of X-rays from the X-ray source is generally monitored by a "reference detector", usually located near the X-ray source.

From measured values of $I_o$ and $I(n,\theta)$ an amount by which X-rays are attenuated along path-length l and a value for the integral $\int\mu(l)dl$, hereinafter referred to as an "absorption integral", can be determined. The attenuation measurement provided by the n-th detector at the view angle $\theta$ therefore provides a value for the line integral of the absorption coefficient along a particular path length through the slice, which is determined by $\theta$ and the known position of the n-th detector relative to the X-ray source.

The set of attenuation measurements for a slice provided by all the detectors in the detector array at a particular view angle $\theta$ is referred to as a view. The set of attenuation measurements from all the views of the slice is referred to as a "projection" of the slice. Values for the absorption integral provided by data from the projection of the slice are processed using algorithms known in the art to provide a map of the absorption coefficient $\mu$ as a function of position in the slice. Maps of the absorption coefficient for the plurality of contiguous slices in the region of the patient's body are used to display and identify internal organs and features of the region.

In some CT-imagers, to image a region of a patient, the region is scanned by moving the patient stepwise in the z direction to "step" the region through the space inside the CT-imager's gantry between the imager's X-ray source and detector array. Following each step, the X-ray source is rotated through 360 degrees or (180+$\Delta$) degrees, where $\Delta$ is an angular width of the fan beam provided by the X-ray source, to acquire a projection of a slice of the region. In some CT-imagers a "spiral scan" of a patient is performed in which the region of the patient is steadily advanced through the gantry while the X-ray source simultaneously rotates around the patient and projections of slices in the region are acquired "on the fly".

In the above discussion it is tacitly assumed that a CT-imager images a single slice of a patient at a time. However, a modern CT-imager is very often a multislice imager that simultaneously images a plurality of slices. Such an (multi-slice) imager comprises a detector array having a plurality of substantially contiguous rows of detectors and the fan beam of the CT-imager is made sufficiently "thick" to illuminate all the rows of detectors. As a result, at any given view angle the CT-imager simultaneously acquires data for a number of slices equal to the number of rows in its detector array. For simplicity of presentation it is generally assumed in the discussion below that a CT-imager is a single slice imager having a detector array comprising a single row of X-ray detectors.

Determining values for the absorption integral from signals generated by X-ray detectors of a CT-imager generally requires performing a calibration procedure in which response of the CT-imager's detectors to X-rays from the imager's X-ray source is measured when nothing is located between the detectors and the X-ray source. Such a calibration procedure is referred to as an "air-calibration".

Let a signal generated by the n-th detector responsive to incident intensity $I(n,\theta)$ be represented by $SI(n,\theta)=g(n,\theta)I(n,\theta)=g(n,\theta)I_o\exp(-\int\mu(l)dl)$ where $g(n,\theta)$ is a proportionality coefficient, hereinafter referred to as a "gain", of the detector. Let a signal generated by the CT-imager's reference detector responsive to X-ray intensity $I_o$ provided by the X-ray source be represented by $RSI_o=g_rI_o$, where $g_r$ is a gain of the reference detector. (In general, $g_r$ of the reference detector is independent of view angle and for convenience this is assumed to pertain in the present discussion so that $g_r$ is written as independent of $\theta$.) The absorption integral is determined from the log of $\{SI(n,\theta)/RSI_o\}$. In particular, $\ln\{SI(n,\theta)/RSI_o\}=\ln\{[g(n,\theta)I_o\exp(-\int\mu(l)dl)]/[g_rI_o]\}=[\ln\{g(n,\theta)/g_r\}-\int\mu(l)dl]$, so that the absorption integral $\int\mu(l)dl=[\ln\{SI(n,\theta)/SI_o\}-\ln\{g(n,\theta)/g_r\}]$.

From the expression for the absorption integral it is seen that to determine a value of the absorption integral from the signals $SI(n,\theta)$ and $RSI_o$ the log of the gain ratio $g(n,\theta)/g_r$ must be determined. Values for the gain ratio $g(n,\theta)/g_r$ of detectors in the detector array are provided by performing an air calibration. During an air calibration, since there is nothing between the X-ray source and the detector array so that $\int \mu(l) dl \cong 0$ and $\ln \{SI(n,\theta)/RSI_o\} = [\ln \{g(n,\theta)/g_r\} - \int \mu(l) dl] = \ln \{g(n,\theta)/g_r\}$.

Generally, in an air-calibration, calibration data (i.e. signals $SI(n,\theta)$ and $RSI_o$ with nothing but air between the X-ray source and detector array) is acquired for a plurality of different view angles $\theta$. The acquired data is processed to provide for each detector an average over a plurality of view angles of the log of the air-calibration gain ratios. It is convenient to represent the view angle average of the logarithm of the air-calibration gain ratio, hereinafter a "gain ratio factor", for the n-th detector by the symbol $AC(n)$ so that $$AC(n) = \overline{\ln\{g(n,\theta)/g_r\}}^{\theta}$$

where the overhead bar followed by $\theta$ represents an average with respect to view angle $\theta$ of the expression under the bar. For each detector, its gain ratio factor $AC(n)$ is used to determine a value for an absorption integral from a signal $SI(n,\theta)$ provided by the detector so that $\int \mu(l) dl = [\ln \{SI(n,\theta)/SI_o\} - AC(n)\}]$.

The $AC(n)$ of a CT-imager can be dependent on values of software and hardware parameters that determine an operating configuration of the CT-imager. As a result, often values $AC(n)$ for a CT-imager are acquired in an air-calibration of the imager for different frequently used operating configurations of the imager. For example, the $AC(n)$ can be functions, inter alia, of an operating voltage of the X-ray source of the CT-imager and configuration of a collimator that collimates X-rays from the X-ray source to determine thickness of slices that the imager images. A full air-calibration of the CT-imager may therefore provide values for gain ratio factors for different X-ray voltages and slice thickness settings.

An air-calibration of a CT-imager may require a period of time that lasts from a few minutes to more than a half-hour to be performed and is often performed only once a day before beginning an "imaging workday" in which the CT-imager is used to image patients. Whereas an air-calibration may be performed as frequently as a few times a day, performing an air-calibration once CT-imaging of patients has begun, increases imager down time and decreases patient throughput.

However, during a day's operation of a CT-imager, gain ratios of detectors in the CT-imager often change as a result of changes in sensitivity of the detectors due, for example, to temperature changes and radiation damage and changes in communication links that transmit data from the detectors mounted on the gantry rotor to the gantry's stator. Such changes can degrade images provided by the CT-imager by, for example, generating ring artifacts in the images.

To provide some measure of adjustment for changes that may occur in gain ratio factors during CT-imaging operation, often an average $$AC = (1/N) \sum_{1}^{N} AC(n)$$

of the gain ratio factors $AC(n)$ is determined, where N is a total number of detectors in the detector array. Each gain ratio factor $AC(n)$ is then usually expressed as a sum $AC(n) = AC + \Delta AC(n)$ where $\Delta AC(n)$, hereinafter a "differential gain ratio factor", is a deviation of the gain ratio factor from the average. During CT-imaging of a region of the body of a patient with a CT-imager, generally, for each view acquired of the region, some of the detectors in the imager's detector array are not shadowed by the patient's body. X-rays from the X-ray source are incident on these non-shadowed detectors without passing through the patient's body. Signals generated by the non-shadowed detectors in the view responsive to X-ray radiation incident thereon are used to determine an average value for the gain ratio factor for the non-shadowed detectors. If the average gain ratio factor for the non-shadowed detectors is statistically significantly different from average gain ratio factor AC, then the "non-shadowed" average gain ratio factor is used to update AC and thereby values of the gain ratio factors $AC(n)$ for the view.

Whereas, values for $AC(n)$ of a CT-imager may be corrected, as noted above, by correcting average gain ratio factors AC responsive to average gain ratios determined for non-shadowed detectors, the corrections thus made do not correct for changes in the differential gain ratio factors $\Delta AC(n)$ of the imager. As a result, quality of CT-images acquired with the imager during a day's operation can be compromised by ring artifacts and other image defects.

It would be advantageous to have a method for updating gain ratio factors $AC(n)$ for a CT-imager during "run time" of the imager, i.e. when the imager is being used to image patients, by updating the imager's differential gain ratio factors without having to perform air-calibration of the imager during run time.

SUMMARY OF THE INVENTION

An aspect of some embodiments of the present invention relates to providing a method for updating values for gain ratio factors of a CT-imager during run time of the imager by updating the imager's differential gain ratio factors without having to perform an air-calibration of the imager.

During normal imaging procedures with a CT-imager, often during a scanning procedure performed to image a patient, for a portion of the procedure, the CT-imager's X-ray source illuminates the detector array when there is nothing located between the X-ray source and the detector array. Absorption data generated during such portions of a scan, hereinafter referred to as "blank portions", provides the same type of as data generated during a conventional air-calibration. In accordance with an embodiment of the present invention the data is used to update the imager's gain ratio factors. Updating is therefore achieved using run time data generated during CT-scans of patients that are normally performed to acquire CT-images of the patients. As a result updating, in accordance with an embodiment of the present invention, does not interfere with or interrupt the normal work-flow of CT-imaging patients and does not increase down time of the imager.

For example, before CT-imaging a region of a patient, generally two pilot scans of the patient are performed to generate data for planning positions of the X-ray source and detector array during subsequent scans of the patient used to image the region. During each pilot scan, the X-ray source is located at a constant view angle as the patient is moved axially through the CT-imager gantry. To assure that all of a patient is scanned, often a pilot scan begins shortly before the patient's body enters the space between the X-ray source and the detector array and/or ends shortly after the patient's body is completely moved out of the space between the X-ray source and the detector array. As a result, often at the end or at the beginning of a pilot scan, neither the patient nor the couch on which the patient is supported protrudes into the space within the gantry between the X-ray source and the detector array and the detectors acquire "blank views". As a result, signals generated by the detectors, at the end or beginning of a pilot scan, when normalized to signals provided by the reference detector, provide measures of the gain ratios of the detectors. In accordance with an embodiment of the present invention, the gain ratio measurements thus acquired are used to update gain ratio factors for the imaging imager's X-ray detectors. Similarly, at the beginning or end of a scan of a person's head, data is usually acquired for a plurality of blank views during which nothing except air is located in the space between the X-ray source and the imager's detector array. Signals provided for these views by the detectors in the detector array provide air-calibration type data that is used, in accordance with an embodiment of the present invention, to update the imaging imager's gain ratio factors.

In some embodiments of the present invention, a scanning procedure used to image a patient is modified to include extra views, which are blank views, in order to acquire data for updating gain ratio factors of a CT-imager. The number and timing of the additional blank views are determined so as to minimize interference with normal work-flow of imaging patients. (It is noted that the addition of blank views, in accordance with an embodiment of the present invention, does not increase the patient's exposure to radiation during the scanning procedure since the blank views are acquired when no part of the patient's body is exposed to X-rays.)

In general, run time "blank" signals are acquired for a particular operating configuration of a CT-imager, namely the operating configuration used in scanning the patient immediately before or immediately after acquiring the blank signals. In some embodiments of the present invention, the blank signals are used to update only the differential gain ratio factors $\Delta AC(n)$ for the particular operating configuration under which the blank signals are acquired. The average gain ratio factor, AC, is updated for views acquired under the particular operating configuration using signals generated by non-shadowed detectors as described above. In some embodiments of the present invention, the blank signals are used to update both the average gain ratio factor and the differential gain ratio factors for the particular operating configuration under which the blank signals are acquired.

In some embodiments of the present invention, for gain ratio factors corresponding to operating configurations different from the particular operating configuration, the run time blank signals are used to update only differential gain ratio factors. The average gain ratio factors for operating configurations different from the particular operating configuration are updated using signals generated by non-shadowed detectors as described above.

Often, changes in temperature during a run time of a CT-imager are a dominant cause of changes in gain ratio factors of detectors in the CT-imager during the run time. An aspect of some embodiments of the present invention relates to providing a method for adjusting values of gain ratio factors of detectors in a CT-imager responsive to changes in gain ratios caused by changes in temperature during run time of the imager.

In accordance with an embodiment of the present invention, an air-calibration of the CT-imager is performed at both a relatively low ambient temperature and a relatively high ambient temperature. The low temperature air-calibration and the high temperature calibration are used to determine an average rate of change, hereinafter referred to as a "temperature derivative", with respect to temperature of the gain ratio factor AC(n) for each of the detectors in the CT-imager.

During subsequent CT-imaging of a patient, signals generated responsive to incident X-rays from the X-ray source by detectors that are not shadowed by the patient are used to determine gain ratio factors for the non-shadowed detectors. The determined gain ratio factors are used to determine an average difference in gain ratio factor for each of the non-shadowed detectors relative to either the low or high temperature gain ratio factor established for the detector. The difference is assumed to result only from a change in temperature and an operating temperature for each of the non-shadowed detectors that is consistent with the difference is determined by interpolation using the temperature derivative of the non-shadowed detector. An average of the determined operating temperatures is used as an estimate of the ambient temperature, hereinafter referred to as a "scan temperature", at which the CT-imager is operating.

The scan temperature and temperature derivatives are used to interpolate values for the gain ratio factors for "shadowed" detectors, which sense X-rays from the X-ray source that have passed through the patient's body. If an interpolated value for a shadowed X-ray detector is statistically significantly different from a current value for the gain ratio factor for the detector, the current value is replaced by the interpolated value. The adjustment of gain ratio factors responsive to scan temperature, in accordance with an embodiment of the present invention, comprehends adjustments to both the average gain ratio factor and the differential gain ratio factors of detectors in the CT-imager.

In some embodiments of the present invention air-calibrations used to perform "temperature adjustments" of gain ratio factors for a CT-imager in a relevant range of ambient operating temperatures are acquired at more than two different temperatures in the range. The air calibrations provide values for the gain ratio factors and temperature derivatives for each X-ray detector of the CT-imager at a plurality of different temperatures in the temperature range. Interpolation of gain ratio factors for a given scan temperature for the CT-imager is performed using air calibration gain ratio factors and temperature derivatives at a temperature of the plurality of temperatures that is closest to the scan temperature. The use of data from air-calibrations at more than two temperatures to adjust gain ratio factors, in accordance with an embodiment of the present invention, can improve accuracy of the adjustments relative to accuracy of adjustments made using data from air-calibrations at only two temperatures. It also enables accurate interpolation to be performed over a wider temperature range than is possible with interpolation performed using data from only two air-calibrations.

Since temperature change is often a dominant cause of change in gain ratio factors of X-ray detectors, substantial effort and cost is generally invested in reducing sensitivity of CT-scanners to temperature change. Providing a reliable and accurate method for adjusting values of gain ratio factors responsive to temperature change, in accordance with an embodiment of the present invention, enables design tolerances for temperature stability of a CT-imager to be relaxed. Therefore, cost of a CT-imager that comprises a processor programmed to perform temperature adjustments of gain ratio factors in accordance with an embodiment of the present invention can generally be reduced relative to cost of a CT-imager that does not comprise such a processor.

It is also noted that algorithms for adjusting gain ratio factors responsive to temperature changes, in accordance with an embodiment of the present invention, that are not linear interpolation algorithms are possible and can be advantageous. For example, dependence of the gain ratio factor of an X-ray detector on temperature can be determined from a best-fit curve, which may be non-linear, that is generated for values of air-calibration gain ratio factors for the detector at more than two temperatures.

There is therefore provided in accordance with an embodiment of the present invention, a method of adjusting values for sensitivities of X-ray detectors comprised in a CT-imager that generate signals responsive to X-rays from an X-ray source in the imager, comprising: acquiring signals generated by X-ray detectors in the CT-imager responsive to X-rays incident thereon from the X-ray source for views taken during a scanning procedure performed by the CT-imager to image a patient when only air is present in a space between the X-ray source and the detectors; and using the signals to adjust the values of the sensitivities.

Optionally the method comprises modifying the scanning procedure to acquire signals from the X-ray detectors for additional views that would not normally be taken during the scanning procedure and for which additional views only air is present in the space between the X-ray source and using the signals acquired in the additional views to adjust the values of the sensitivities.

Alternatively or additionally adjusting values of sensitivities comprises adjusting values of differential sensitivities of the X-ray detectors, wherein a differential sensitivity of an X-ray detector is a difference between the sensitivity of the detector and an average sensitivity for all the X-ray detectors.

Optionally, adjusting values of differential sensitivities comprises: determining a sensitivity for each of the X-ray detectors from the signals; determining an average sensitivity for the X-ray detectors from the determined sensitivities; determining a difference sensitivity for each X-ray detector which is equal to a difference between the determined average sensitivity and the sensitivity of the X-ray detector determined from the signals; and replacing the value of differential sensitivity with the value of the difference sensitivity.

Optionally replacing the differential sensitivity comprises: determining if a difference between the difference sensitivity and the differential sensitivity for the X-ray detector is statistically significant as determined with reference to a predetermined test of significance; and replacing the differential sensitivity with the difference sensitivity only if the difference is statistically significant.

In some embodiments of the present invention the scanning procedure is performed for a first configuration of operating parameters for the CT-imager that determine characteristics of the scanning procedure and comprising using the signals to adjust values of the sensitivities for operation of the CT-imager for a second different configuration of the operating parameters.

There is further provided, in accordance with an embodiment of the present invention, a method of adjusting values for sensitivities of X-ray detectors comprised in a CT-imager that generate signals responsive to X-rays from an X-ray source in the imager, comprising: measuring sensitivities for each X-ray detector in the CT imager at a plurality of different temperatures; determining an ambient temperature at which a scan of a patient is performed with the CT-imager; determining a value for the sensitivity of an X-ray detector at the ambient temperature using the ambient temperature and measured sensitivities for the X-ray detector at at least two of the plurality of temperatures; and replacing the value of the sensitivity of the X-ray detector with the value of the ambient temperature sensitivity.

Optionally, determining an ambient temperature comprises: acquiring signals from at least one X-ray detector in the CT-imager during a scan of a patient when the detector is not shadowed from the X-ray source by the patient's body; determining a sensitivity for the at least one X-ray detector using the acquired signals; determining a value for an operating temperature of each of the at least one X-ray detector using the sensitivity determined from the signals and measured sensitivities at at least two of the plurality of temperatures; and determining an ambient temperature from operating temperatures of the X-ray detectors.

Optionally, determining a value for an operating temperature of the at least one X-ray detector comprises interpolating the value.

Additionally or alternatively, the at least one X-ray detector optionally comprises a plurality of X-ray detectors.

Optionally, determining a value for the ambient temperature comprises determining the ambient temperature to be equal to an average of operating temperatures.

Optionally, determining the average comprises determining which of the operating temperatures are statistically significant responsive to a predetermined test of significance and determining the average to be equal to the average of the operating temperatures determined to be statistically significant.

In some embodiments of the present invention, the ambient temperature is not determined using signals generated by the X-ray detector whose ambient temperature sensitivity is determined.

In some embodiments of the present invention, determining a value for the sensitivity of the X-ray detector at the ambient temperature comprises interpolating an operating temperature for the at least one detector.

In some embodiments of the present invention, replacing the value for the sensitivity of the X-ray detector comprises: determining if a difference between the sensitivity of the X-ray detector and the ambient temperature sensitivity of the X-ray detector is statistically significant as determined with reference to a predetermined test of significance; and replacing the value of the sensitivity with the ambient temperature sensitivity only if the difference is statistically significant.

In some embodiments of the present invention, the sensitivity of an X-ray detector in the CT-imager is defined to be equal to the log of the ratio of the gain of the X-ray detector divided by a gain of a reference detector in the imager that measures intensity of X-rays provided by the X-ray source.

There is further provided a CT-imager comprising a processor programmed to adjust values for sensitivities of X-ray detectors comprised in the CT-imager in accordance with any of the preceding claims.

There is further provided, in accordance with an embodiment of the present invention, a CT-imager for imaging a patient comprising an X-ray source and X-ray detectors that generate signals responsive to X-rays from the X-ray source, the CT-imager additionally comprising: a memory that stores a value for the sensitivity of each detector, which sensitivity value is used to process signals from the detector so as to provide an image of the patient; a controller that positions the imager so that during a scanning procedure of the patient the detectors are exposed to X-rays from the X-ray source and generate signals responsive to the X-rays to which they are exposed when only air is located between the X-ray source and the detectors; a processor that processes signals generated by the detectors when only air is present between the X-ray source and the detectors to adjust sensitivity values of the detectors that are stored in the memory.

Optionally, the controller modifies the scanning procedure to add views thereto that would not normally be taken during the procedure, for which additional views only air is present in the space between the X-ray source and the detectors generate signals that are used by the processor for adjusting values of the sensitivities.

Additionally or alternatively, the processor optionally adjusts values of sensitivities by adjusting values of differential sensitivities of the X-ray detectors, wherein a differential sensitivity of an X-ray detector is a difference between the sensitivity of the detector and an average sensitivity for all the X-ray detectors.

Optionally, an algorithm by which the processor adjusts differential sensitivities comprises: determining a sensitivity for each of the X-ray detectors from the signals; determining an average sensitivity for the X-ray detectors from the determined sensitivities; determining a difference sensitivity for each X-ray detector which is equal to a difference between the determined average sensitivity and the sensitivity of the X-ray detector determined from the signals; and replacing the value of differential sensitivity with the value of the difference sensitivity.

Optionally, replacing the differential sensitivity comprises: determining if a difference between the difference sensitivity and the differential sensitivity for the X-ray detector is statistically significant as determined with reference to a predetermined test of significance; and replacing the differential sensitivity with the difference sensitivity only if the difference is statistically significant.

In some embodiments of the present invention, the scanning procedure is performed for a first configuration of operating parameters for the CT-imager that determine characteristics of the scanning procedure and the processor uses the signals to adjust values of the sensitivities for operation of the CT-imager for a second, different configuration of the operating parameters.

There is further provided, in accordance with an embodiment of the present invention, a CT-imager for imaging a patient comprising an X-ray source and X-ray detectors that generate signals responsive to X-rays from the X-ray source, the CT-imager additionally comprising: a memory that stores for each detector a value for a reference sensitivity at each of a plurality of different temperatures and an operating sensitivity, which operating sensitivity is used to process signals from the detector so as to provide an image of the patient; means for determining an ambient temperature at which a scan of the patient is performed with the CT-imager; and a processor that uses the ambient temperature and the reference sensitivities for an X-ray detector at at least two of the plurality of temperatures to determine a value for the sensitivity of the X-ray detector at the ambient temperature and replaces the stored value for the operating sensitivity with the determined ambient temperature sensitivity.

Optionally, the means for determining the ambient temperature comprises a processor that determines the ambient temperature in accordance with an algorithm that comprises: acquiring signals from at least one X-ray detector in the CT-imager during the scan of the patient when the detector is not shadowed from the X-ray source by the patient's body; determining a sensitivity for the at least one X-ray detector using the acquired signals; determining a value for an operating temperature of each of the at least one X-ray detector using the sensitivity determined from the signals and reference sensitivities at at least two of the plurality of temperatures; and determining an ambient temperature from operating temperatures of the X-ray detectors.

Optionally, determining a value for an operating temperature of the at least one X-ray detector comprises interpolating the value.

Additionally or alternatively, the at least one X-ray detector optionally comprises a plurality of X-ray detectors.

Optionally, determining a value for the ambient temperature comprises determining the ambient temperature to be equal to an average of operating temperatures.

Optionally, determining the average comprises determining which of the operating temperatures are statistically significant responsive to a predetermined test of significance and determining the average to be equal to the average of the operating temperatures determined to be statistically significant.

In some embodiments of the present invention, the ambient temperature is not determined using signals generated by the X-ray detector whose ambient temperature sensitivity is determined.

In some embodiments of the present invention, the processor determines a value for the sensitivity of the X-ray detector at the ambient temperature by interpolating an operating temperature for the at least one detector.

In some embodiments of the present invention, replacing the value for the sensitivity of the X-ray detector comprises: determining if a difference between the sensitivity of the X-ray detector and the ambient temperature sensitivity of the X-ray detector is statistically significant as determined with reference to a predetermined test of significance; and replacing the value of the sensitivity with the ambient temperature sensitivity only if the difference is statistically significant.

In some embodiments of the present invention, the sensitivity of an X-ray detector in the CT-imager is defined to be equal to the log of the ratio of the gain of the X-ray detector divided by a gain of a reference detector in the imager that measures intensity of X-rays provided by the X-ray source.

BRIEF DESCRIPTION OF FIGURES

Non-limiting examples of embodiments of the present invention are described below with reference to figures attached hereto. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale. The figures are listed below.

DETAILED DESCRIPTION OF EXEMPLARY EMBODIMENTS

Figure 1:
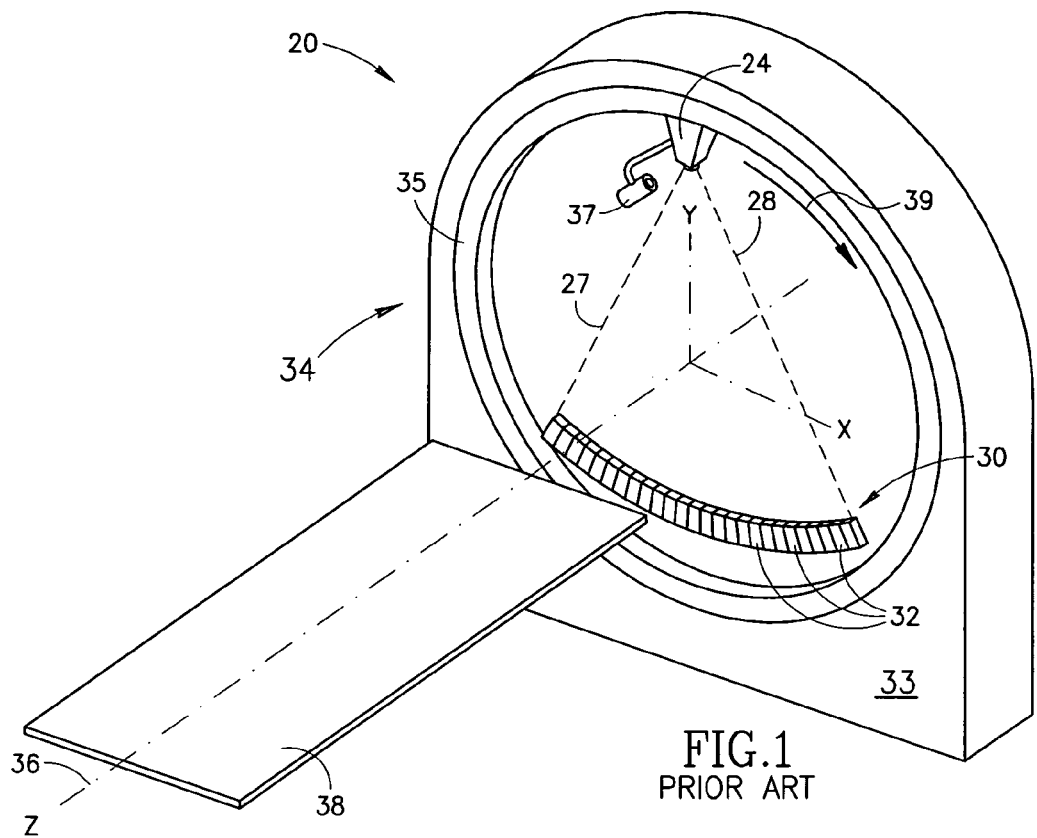
FIG. 1 schematically shows a CT-imager being air-calibrated to determine gain ratio coefficients for the CT-imager, in accordance with prior art.

FIG. 1 schematically shows a CT-imager 20 being air-calibrated to determine gain ratio factors, in accordance with prior art.

CT-imager 20 comprises an X-ray source 24 controllable to provide a fan-beam schematically indicated by dashed lines 27 and 28 and an array 30 of X-ray detectors 32 opposite the X-ray source for sensing X-rays in the fan-beam. CT-imager 20 comprises a gantry 34 having a stator 33 to which a rotor 35 is mounted so that the rotor can be controlled to rotate about an axis 36. X-ray source 24 and detector array 30 are rigidly mounted to rotor 35 so that when rotor 35 rotates about axis 36 the X-ray source and detector array also rotate about the axis. CT-imager 20 is shown, by way of example, as a single slice imager and array 30 has, accordingly, a single row of detectors in array 30. It is noted however that the present invention is not limited to single slice CT-imagers. Embodiments of the present invention may be practiced with multi-slice CT-scanners for which array 30 would have a plurality of rows of detectors 32, as well as single slice scanners.

A reference detector 37 mounted optionally near X-ray source 24 receives X-rays directed from the X-ray source to the reference detector using methods known in the art and generates signals $RSI_o$ proportional to intensity $I_o$ of X-rays provided by the X-ray source. A couch 38 mounted on a suitable pedestal (not shown) for supporting a patient during CT-imaging of a region of the patient's body is positioned so that it does not protrude into the space within rotor 35 between X-ray source 24 and detector array 30.

For convenience, a coordinate system is shown in FIG. 1 (and in FIGS. 2 through 3B) having a horizontal x-axis, a vertical y-axis and a z-axis coincident with axis 36. The coordinate system is used to locate components and features of CT-imager 20 and features of a patient imaged with the CT-imager. The coordinate system is assumed to be fixed with respect to gantry 34. View angle of X-ray source 24 is measured with respect to the y-axis of the coordinate system. Slices of the body of a patient lying on couch 38 that are to be imaged with CT-imager 20 are positioned to be exposed to X-rays from X-ray source 24 by moving couch 38 axially along the z-axis. Only components and features of CT-imager 20 germane to the discussion of the invention are shown.

To perform the air-calibration and determine gain ratio factors AC(n) for detectors 32 of CT-imager 20, X-ray source 24 is controlled to provide X-rays at a desired intensity and the X-ray source and detector array 32 are optionally rotated through 360° to acquire views at a plurality of view angles. Curved arrow 39 schematically represents rotating X-ray source 24 and detector array 30.

Let the view angles at which views are acquired be represented by $\theta_k$, where k is an index that defines each of K different view angles at which air-calibration data is acquired. Then the gain ratio factor AC(n) for the n-th detector 32 may be written, $$AC(n) = (1/K)\sum_{k=1}^{K} \ln(SI(n, \theta_k)/RSI_O),$$

where $SI(n,\theta_k)$ is a signal generated by the n-th detector responsive to intensity of X-rays incident on the detector at view angle $\theta_k$.

As noted above, in prior art, a gain ratio factor AC(n) for an X-ray detector in a CT-imager is sometimes expressed as a sum AC(n)=AC+ΔAC(n) where AC is an average gain ratio factor for all detectors in the CT-imager and ΔAC(n) is a differential gain ratio factor for the detector. Adjustments to update values for the gain ratio factors AC(n) of the CT-imager during run time of the CT-imager are made, in accordance with prior art, by updating the average gain ratio factor, AC, as described above.

In general, gain ratio factors AC(n) are different for different operating configurations that define operating parameters of a CT-imager and gain ratio factors for a CT-imager are often determined as functions of parameters that define operating configurations of the CT-imager. For example, gain ratio factors of a CT-imager may be dependent on X-ray source voltage and slice thickness and a gain ratio factor for the n-th detector may therefore be written AC(n, V, τ), where V represents the X-ray source voltage and τ the slice thickness. The gain ratio factors may also be substantially different for different ranges of view angles, as a result for example of shifts in alignment of the CT-imager's detector array relative to the X-ray source as a function of view angle. When this is the case, gain ratio factors for detectors in a CT-imager may also be determined as functions of view angle ranges. For example a possible 360° range of view angles may be divided into 90° degree quadrants and gain ratio factors determined for each quadrant. In the discussion below, dependence of gain ratio factors of a CT-imager on operating configurations of the imager and view angle ranges is not explicitly shown.

Figure 2:
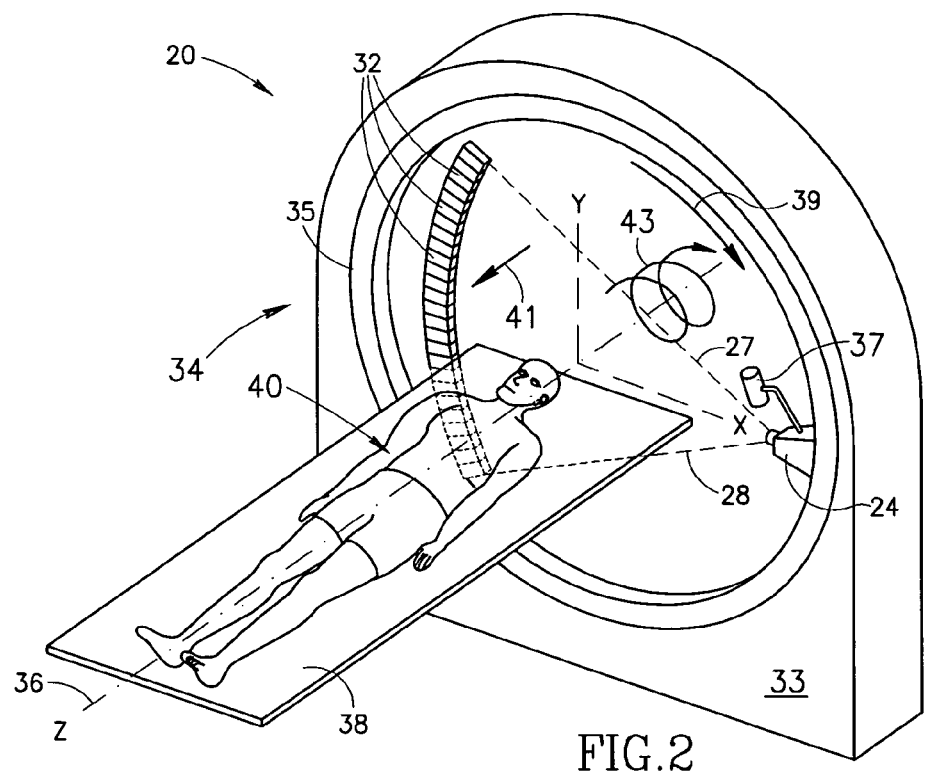
FIG. 2 schematically shows the CT-imager shown in FIG. 1 being operated to acquire data for updating gain ratio factors, in accordance with an embodiment of the present invention.

FIG. 2 schematically shows a method for updating gain ratio factors AC(n)=AC+ΔAC(n) during run time of CT-imager 20 shown in FIG. 1. In FIG. 2, CT-imager 20 is shown completing a spiral scan of the head of a patient 40 and the gain ratio factors AC(n) correspond to an operating configuration used to perform the spiral head scan. For convenience and clarity of presentation, detectors 32 that are located behind couch 36 and patient 40, and would therefore normally not be seen in the perspective of FIG. 2, are shown in ghost lines.

During the spiral scan, couch 38 is translated in the z direction so as to move the patient's head through the space in rotor 35 between X-ray source 24 and detector array 30 while the X-ray source and detector array rotate around the patient to acquire views of the patient's head. Optionally, the patient's head is moved in a direction from the patient's chin towards the top of the patient's head. Arrow 41 schematically indicates direction of motion of couch 38 and corkscrew arrow 43 schematically indicates motion of X-ray source 24 relative to patient 40 during the spiral scan.

After the patient's head has been completely removed from the space in the rotor 35 between X-ray source 24 and detector array 30 by axial translation of couch 38, CT-imager 20 continues, generally as a normal part of the scan, to execute a spiral scan for an additional, relatively short, period of time. During the additional period nothing except air is located between X-ray source 24 and detectors 32 generate, run time, blank signals responsive to intensity of X-ray radiation to which they are exposed. The run time blank signals are used, in accordance with an embodiment of the present invention, to update values of gain ratio factors AC(n) of CT-imager 20. (Determining when the patient's head is no longer in the space between X-ray source 24 and detector array 30 may be accomplished by analyzing output signals from detectors 32. For example output signals of each detector may be compared to a reference signal for the detector provided by an air calibration of the CT-scanner. If a difference in signals from each of detectors 32 and its respective reference signal is less than a predetermined difference, then it is determined that there is nothing between the X-ray source 24 and detector array 30.)

In some embodiments of the present invention, the head scan of a patient is modified to increase the additional period of time after the patent's head is moved out from the rotor during which blank scans are acquired is increased. The increased additional "blank time" results in an increase in the number of blank signals acquired from the detectors, which improves statistical significance of data generated from the signals. Assume that run time blank signals are acquired for each detector 32 for each of J sets of coordinates, $\theta_j$ and $z_j$, $1 \leq j \leq J$, where $\theta_j$ and $z_j$ are a view angle and axial position respectively at which a run time blank signal is generated. Let the run time blank signal generated at $\theta_j$ and $z_j$ by the n-th detector be represented by RTSI(n,$\theta_j$,$z_j$). In accordance with an embodiment of the present invention, a run time gain ratio factor "RTAC(n)" is determined for the n-th detector 32, which is defined by the equation $$RTAC(n) = (1/J) \sum_{1}^{J} \ln(RTSI(n, \theta_j, z_j)/RSI_O).$$

An average run time gain ratio factor for all N detectors 32, "RTAC" is also determined where $$RTAC = \sum_{1}^{N} RTAC(n).$$

For each detector 32, a deviation of its run time gain ratio factor RTAC(n) from the average run time gain ratio factor RTAC is determined to provide a run time differential gain ratio factor $\Delta$RTAC(n)=RTAC(n)−RTAC.

In accordance with an embodiment of the present invention, if a difference between a current value for $\Delta$AC(n) and a value for $\Delta$RTAC(n) is statistically significant, then the current value for $\Delta$AC(n) is updated by replacing the value with the value of $\Delta$RTAC(n).

In some embodiments of the present invention, if a difference between the average gain ratio factor AC and the average run time gain ratio factor RTAC is statistically significant, a current value for AC is adjusted responsive to a value of RTAC to provide an updated value for AC. In some embodiments of the present invention, the value for AC is updated by replacing its current value with the value of RTAC.

In the above discussion, run time gain ratio factors RTAC(n) are acquired for a same operating configuration of CT-imager 20 for which gain ratio factors AC(n) are defined. Values for AC(n) are updated responsive to run time gain ratio factors RTAC(n) that are defined for an operating configuration that is the same as the operating configuration for which the AC(n) are defined, i.e. the operating configuration used to image the head of patient 40.

In some embodiments of the present invention, run time differential gain ratio factors determined for a first operating configuration are used to update differential gain ratio factors defined for a different, second operating configuration. This is optionally done, in accordance with an embodiment of the present invention, when during normal imaging of patients with a CT-imager, for example when imaging the abdomen of patients, portions of scans performed under the second operating configuration are not conveniently available for determining run time gain ratio factors for the second operating configuration.

It is noted that whereas in the above description $g_r$ has been assumed to be independent of $\theta$, the present invention is not limited to the case for which $g_r$ is independent of $\theta$, and that the methods of the present invention are applicable to situations for which $g_r$ is dependent on $\theta$.

Figure 3A:
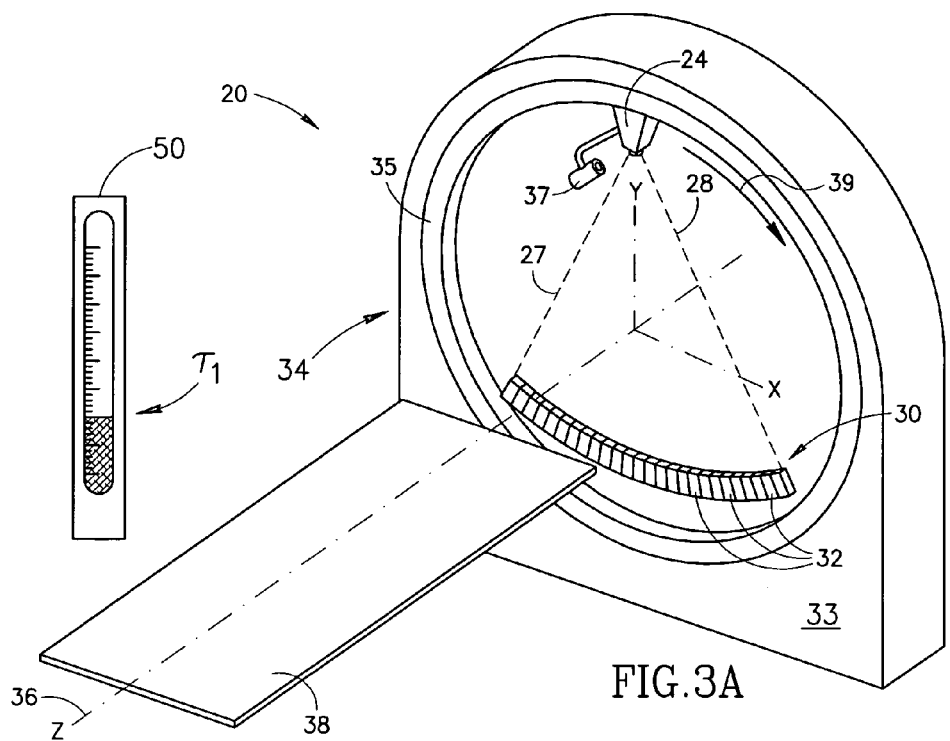
FIGS. 3A-3C schematically illustrate updating gain ratio factors for the CT-imager shown in FIG. 1 responsive to changes in ambient temperature of the environment of the CT-imager, in accordance with an embodiment of the present invention.
Figure 3B:
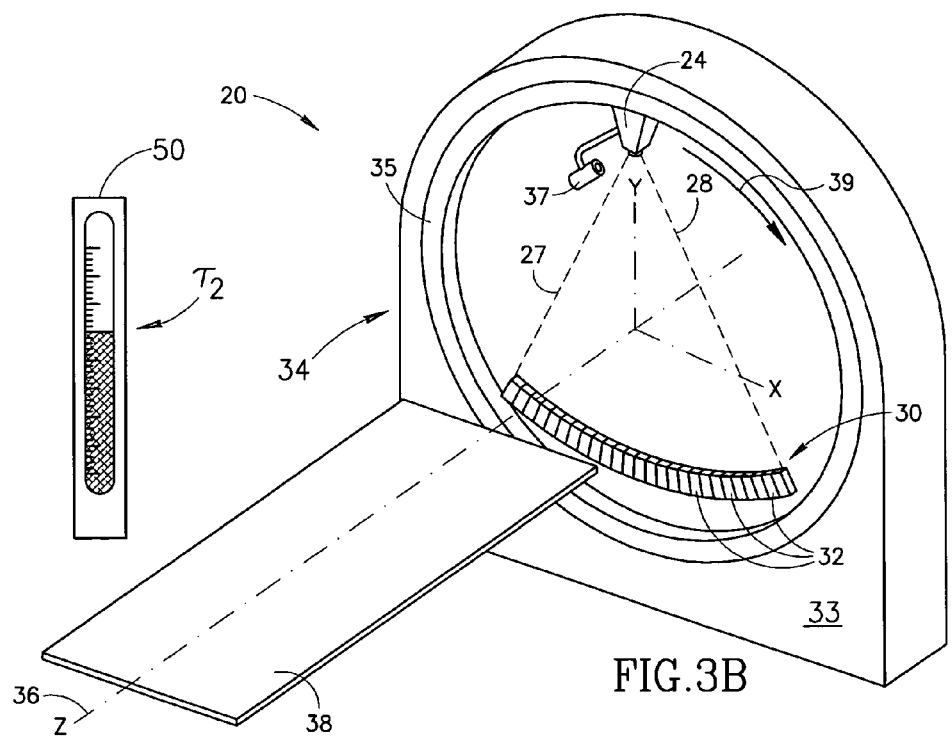

FIGS. 3A and 3B schematically illustrate another method for updating gain ratio factors for an operating configuration of CT-imager 20 shown in FIG. 1 during run time operation of the CT-imager, in accordance with an embodiment of the present invention. Updating is performed responsive to changes in ambient temperature, in accordance with an embodiment of the present invention.

The method comprises acquiring air-calibration gain ratio factors for the operating configuration of CT-imager 20 using a conventional air-calibration procedure for first and second different ambient temperatures $\tau_1$ and $\tau_2$ where $\tau_1 < \tau_2$. FIGS. 3A and 3B schematically show acquiring the gain ratio factors at temperatures $\tau_1$ and $\tau_2$ respectively, which are indicated on a thermometer 50.

Let the set of gain ratio factors acquired for temperatures $\tau_1$ and $\tau_2$ of the operating configuration be represented by AC(n,$\tau_1$) and AC(n,$\tau_2$) respectively. In accordance with an embodiment of the present invention, for each detector 32, an average first derivative $\overline{dAC(n)/d\tau}$ of its gain ratio factor with respect to temperature $\tau$ is estimated for the temperature range $\tau_1$ to $\tau_2$ as being equal to [AC(n,$\tau_2$)−AC(n,$\tau_1$)]/[$\tau_2$−$\tau_1$].

Figure 3C:
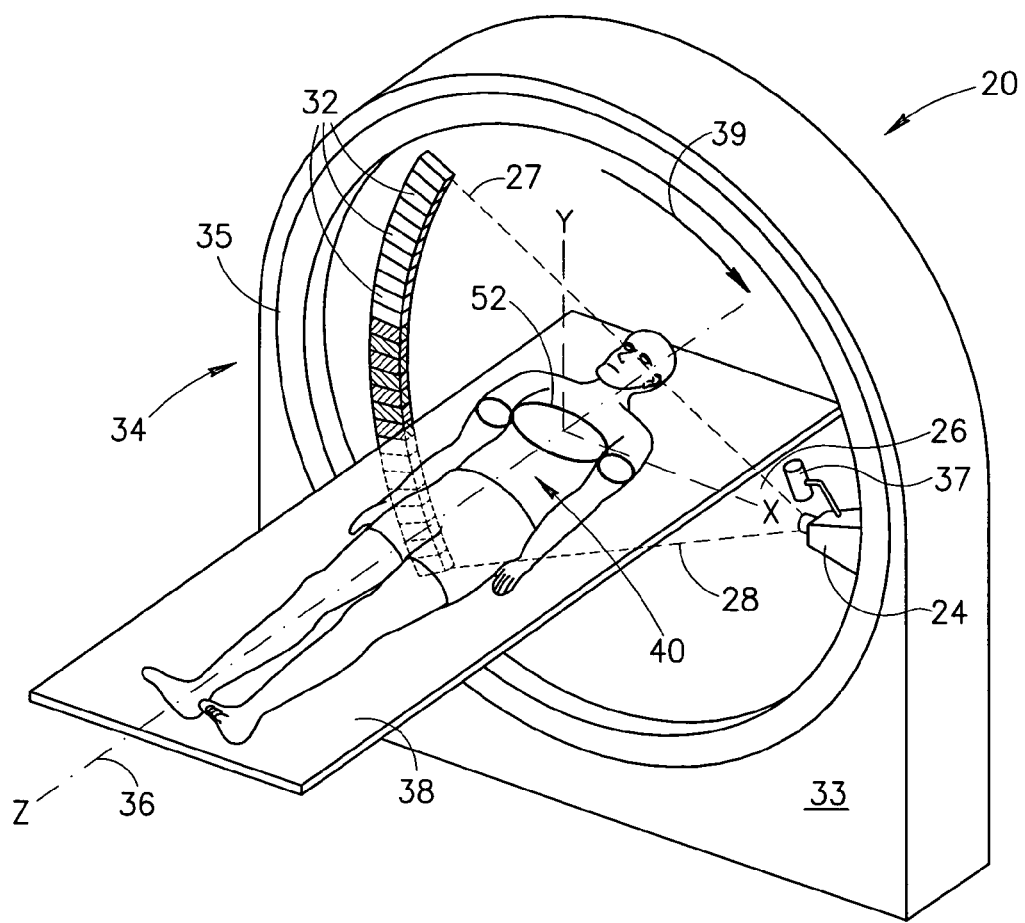

During a scan of a patient 40 performed by CT-imager 20 with the CT-imager set to the operating configuration, for each view taken of the patient, generally some of detectors 32 in the imager are not shadowed by the patient's body and some of detectors 32 are shadowed by the patient's body. For example, FIG. 3C schematically shows CT-imager 20 during the scan of patient 40 acquiring a view of a slice 52 in a region of the chest of the patient. Detectors 32 that are shadowed by slice 52, and which therefore measure intensity of X-rays from X-ray source 24 that pass through slice 52, are shown shaded. Non-shadowed detectors 32 that measure intensity of X-rays from X-ray source 24 that do not pass through slice 52 are shown not shaded. It is noted that some detectors 32 may not be shadowed in any of the views taken during the scan of patient 40. Some detectors 32 may be shadowed in some of the views but not in other views, while some detectors 32 will be shadowed in all the views.

Signals generated by each detector 32, if and when it is not shadowed during the scan of patient 40 are used to determine an average for the log of the gain ratio for the detector, which average defines a run time gain ratio factor RTAC(n) for the detector, where n is the detector index. The average for a particular non-shadowed detector 32 (whether never or only sometimes shadowed during the scan) is optionally taken over all views acquired during the scan for which the particular detector is not shadowed. Run time gain ratio factors that are not statistically significant, as determined responsive to an appropriate statistical criterion, are discarded and statistically significant run time gain ratio factors are retained. Let the index denoting specific detectors 32 for which run time gain ratio factors are determined and retained be represented by n* and let their respective retained run time gain ratio factors be represented by RTAC(n*). Detectors 32 for which a run time gain ratio factor is not established will continue to be denoted by the index n.

For each n*-th detector 32, an ambient operating temperature is determined using the detector's temperature derivative. If $\tau_a$(n*) represents the ambient temperature determined for the n*-th non-shadowed detector 32 then in accordance with an embodiment of the present invention, a value for $\tau_a$(n*) is determined in accordance with an interpolation equation $\tau_a(n^*) = \{[RTAC(n^*) - AC(n^*\tau_1)]/\overline{dAC(n^*)/d\tau} + \tau_1\}$. An average of all the $\tau_a$(n*) is defined as a scan temperature $\tau_a$ for the scan.

In accordance with an embodiment of the present invention, for each n-th detector 32 for which a run time gain ratio factor RTAC(n) is not established, an interpolated gain ratio factor AC'(n) is determined in accordance with a relation AC'(n)=[AC(n,$\tau_1$)+[$\tau_a$−$\tau_1$]$\overline{dAC(n)/d\tau}$]. If a difference between AC(n) and AC'(n) is statistically significant, the value of AC(n) is updated by replacing the value of AC(n) with the value of AC'(n). In accordance with an embodiment of the present invention, the gain ratio factor AC(n*) for each n*-th detector 32 is updated by replacing the value of AC(n*) with the value determined for the run time gain ratio factor RTAC*(n*) of the detector.

It is noted that in the above description two air-calibration procedures are performed to determine a single average temperature derivative for each X-ray detector 32 in the range of ambient operating temperatures $\tau_1$ to $\tau_2$. In some embodiments of the present invention air-calibrations are performed at more than two temperatures in a range of ambient operating temperatures of a CT-imager. The more than two temperatures at which the air-calibrations are preformed divide the temperature range into at least two sub-ranges. For each sub-range an average temperature derivative for each X-ray detector in the CT-imager is determined. In accordance with an embodiment of the present invention, to determine interpolated gain ratio factors for the X-ray detectors for a given scan temperature, the temperature derivatives of the detectors for the sub-range that includes the scan temperature are used. The use of a plurality of temperature sub-ranges and temperature coefficients defined for the X-ray detectors for each of the sub-ranges can improve accuracy of "temperature" adjustments of gain ratio factors relative to accuracy of adjustments determined when a temperature range is not divided into sub-ranges.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. A method of adjusting values for sensitivities of X-ray detectors comprised in a CT-imager that generate signals responsive to X-rays from an X-ray source in the imager, comprising:
   acquiring signals generated by X-ray detectors in the CT-imager responsive to X-rays incident thereon from the X-ray source for views taken during a scanning procedure performed by the CT-imager to image a patient when only air is present in a space between the X-ray source and the detectors; and
   using the signals to adjust the values of the sensitivities.

2. A method according to claim 1 and comprising modifying the scanning procedure to acquire signals from the X-ray detectors for additional views that would not normally be taken during the scanning procedure and for which additional views only air is present in the space between the X-ray source and the detectors and using the signals acquired in the additional views to adjust the values of the sensitivities.

3. A method according to claim 1 wherein adjusting values of sensitivities comprises adjusting values of differential sensitivities of the X-ray detectors, wherein a differential sensitivity of an X-ray detector is a difference between the sensitivity of the detector and an average sensitivity for all the X-ray detectors.

4. A method according to claim 3 wherein adjusting values of differential sensitivities comprises:
   determining a sensitivity for each of the X-ray detectors from the signals;
   determining an average sensitivity for the X-ray detectors from the determined sensitivities;
   determining a difference sensitivity for each X-ray detector which is equal to a difference between the determined average sensitivity and the sensitivity of the X-ray detector determined from the signals; and
   replacing the value of differential sensitivity with the value of the difference sensitivity.

5. A method according to claim 4 wherein replacing the differential sensitivity comprises:
   determining if a difference between the difference sensitivity and the differential sensitivity for the X-ray detector is statistically significant as determined with reference to a predetermined test of significance; and
   replacing the differential sensitivity with the difference sensitivity only if the difference is statistically significant.

6. A method according to claim 1 wherein the scanning procedure is performed for a first configuration of operating parameters for the CT-imager that determine characteristics of the scanning procedure and comprising using the signals to adjust values of the sensitivities for operation of the CT-imager for a second different configuration of the operating parameters.

7. A CT-imager for imaging a patient comprising an X-ray source and X-ray detectors that generate signals responsive to X-rays from the X-ray source, the CT-imager additionally comprising:
   a memory that stores a value for the sensitivity of each detector, which sensitivity value is used to process signals from the detector so as to provide an image of the patient;
   a controller that positions the imager so that during a scanning procedure of the patient the detectors are exposed to X-rays from the X-ray source and generate signals responsive to the X-rays to which they are exposed when only air is located between the X-ray source and the detectors; and
   a processor that processes signals generated by the detectors when only air is present between the X-ray source and the detectors to adjust sensitivity values of the detectors that are stored in the memory.

8. A CT-imager according to claim 7 wherein the controller modifies the scanning procedure to add views thereto that would not normally be taken during the procedure, for which additional views only air is present in the space between the X-ray source and the detectors and the detectors generate signals that are used by the processor for adjusting values of the sensitivities.

9. A CT-imager according to claim 7 wherein the processor adjusts values of sensitivities by adjusting values of differential sensitivities of the X-ray detectors, wherein a differential sensitivity of an X-ray detector is a difference between the sensitivity of the detector and an average sensitivity for all the X-ray detectors.

10. A CT-imager according to claim 9 wherein an algorithm by which the processor adjusts differential sensitivities comprises:

determining a sensitivity for each of the X-ray detectors from the signals;

determining an average sensitivity for the X-ray detectors from the determined sensitivities;

determining a difference sensitivity for each X-ray detector which is equal to a difference between the determined average sensitivity and the sensitivity of the X-ray detector determined from the signals; and replacing the value of differential sensitivity with the value of the difference sensitivity.

11. A CT-imager according to claim 10 wherein replacing the differential sensitivity comprises:

determining if a difference between the difference sensitivity and the differential sensitivity for the X-ray detector is statistically significant as determined with reference to a predetermined test of significance; and replacing the differential sensitivity with the difference sensitivity only if the difference is statistically significant.

12. A CT-imager according to claim 7 wherein the scanning procedure is performed for a first configuration of operating parameters for the CT-imager that determine characteristics of the scanning procedure and the processor uses the signals to adjust values of the sensitivities for operation of the CT-imager for a second, different configuration of the operating parameters.

13. The CT-imager according to claim 7 wherein the sensitivity of an X-ray detector in the CT-imager is defined to be equal to the log of the ratio of the gain of the X-ray detector divided by a gain of a reference detector in the imager that measures intensity of X-rays provided by the X-ray source.

* * * * *